(12) United States Patent
Boyle

(10) Patent No.: US 7,741,486 B1
(45) Date of Patent: Jun. 22, 2010

(54) WATER-SOLUBLE TITANIUM ALKOXIDE MATERIAL

(75) Inventor: Timothy J Boyle, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 12/406,449

(22) Filed: Mar. 18, 2009

Related U.S. Application Data

(60) Provisional application No. 61/037,755, filed on Mar. 19, 2008.

(51) Int. Cl.
*C07F 7/28* (2006.01)
*C07D 213/02* (2006.01)
(52) U.S. Cl. .............................. 546/6; 556/56
(58) Field of Classification Search .............. 546/6; 556/56
See application file for complete search history.

(56) References Cited

U.S. PATENT DOCUMENTS 7,256,290 B1    8/2007   Boyle

OTHER PUBLICATIONS

Potter, B.G. et al.: Photo-initiation of intermolecular bonding and oxide deposition in Ti-based alkoxide solutions. J. of non-crystalline solids, vol. 354, pp. 2017-2022, 2008.*
Boyle, T.J., Sewell, R.M., Ottley, L.A.M., Pratt III, H.D, Qunitana, C.J., and Bunge, S.D., "Controlled Synthesis of a Structurally Characterized Family of Sterically Constrained Heterocylcylic Alkoxy-Modified Titanium Alkoxides,", Inorg. Chem. 2007, 46, 1825-1835.

* cited by examiner

*Primary Examiner*—Charanjit S Aulakh
(74) *Attorney, Agent, or Firm*—Elmer A. Klavetter

(57) ABSTRACT

A water soluble, water stable, titanium alkoxide composition represented by the chemical formula $(OC_6H_6N)_2Ti(OC_6H_2(CH_2N(CH_3)_2)_3\text{-}2,4,6)_2$ with a theoretical molecular weight of 792.8 and an elemental composition of 63.6% C, 8.1% H, 14.1% N, 8.1% O and 6.0% Ti.

5 Claims, 2 Drawing Sheets

WATER-SOLUBLE TITANIUM ALKOXIDE MATERIAL

RELATED APPLICATIONS

This application claims the benefit of U.S. Provisional Application No. 61/037,755, filed on Mar. 19, 2008.

This invention was made with Government support under Contract No. DE-AC04-94AL85000 awarded by the Department of Energy. The Government has certain rights in the invention.

BACKGROUND OF THE INVENTION

The present invention relates generally to metal alkoxide compounds and more particularly to a water-soluble, water-stable, titanium alkoxide compound of the formula $(OC_6H_6N)_2Ti(OC_6H_2(CH_2N(CH_3)_2)_3-2,4,6)_2$.

Metal alkoxides $(M(OR)_x)$ are excellent precursors for the preparation of ceramic oxide materials and have applications ranging from electro-active ceramics, conductors, semiconductors, and catalysts. The structural arrangement of the precursor has been shown to play a significant role in determining the properties of the final materials. Unfortunately, controlling the structure of even the simplest $M(OR)_x$ species has not been realized; therefore, predicting the final structure of complex, mixed-ligand $M(OR)_x$ species is not yet possible. The variable noted for $M(OR)_x$ species is often attributed to the small charge to large cation radius ratio that requires the metal to bind additional ligands (i.e., bridging) to complete their coordination sphere. This phenomenon leads to uncontrolled cluster formation. In addition, the ligands often decompose to form oxides and unexpected structural rearrangements are often reported for supposed simple modification to $M(OR)_x$. In particular, water-soluble, water-stable titanium alkoxide compounds would be of utility.

In order to minimize the oligomerization behavior of $M(OR)_x$, a number of bulky ligands have been introduced to fill coordination sites without depleting the charge of the metal. Of these, the monodentate tert-butyloxide is considered one of the more sterically demanding ligands available and is often used to limit oligomerization although oligomers still predominate compared with produced monomeric species. One alkoxide ligand that has been successfully used to reduce clustering was tetrahydrofurfuryl alcohol (H-OTHF). The bidentate H-OTHF ligand is constructed in such a manner that it will preferentially chelate due to the non-charged Lewis bind site of the heterocycle THF. Other ligands that have been used include the thiophene methanol (H-OTPM) and pyridine methanol or 2-pyridylcarbinol (H-OPy) ligands.

DETAILED DESCRIPTION OF THE INVENTION

Figure 1:
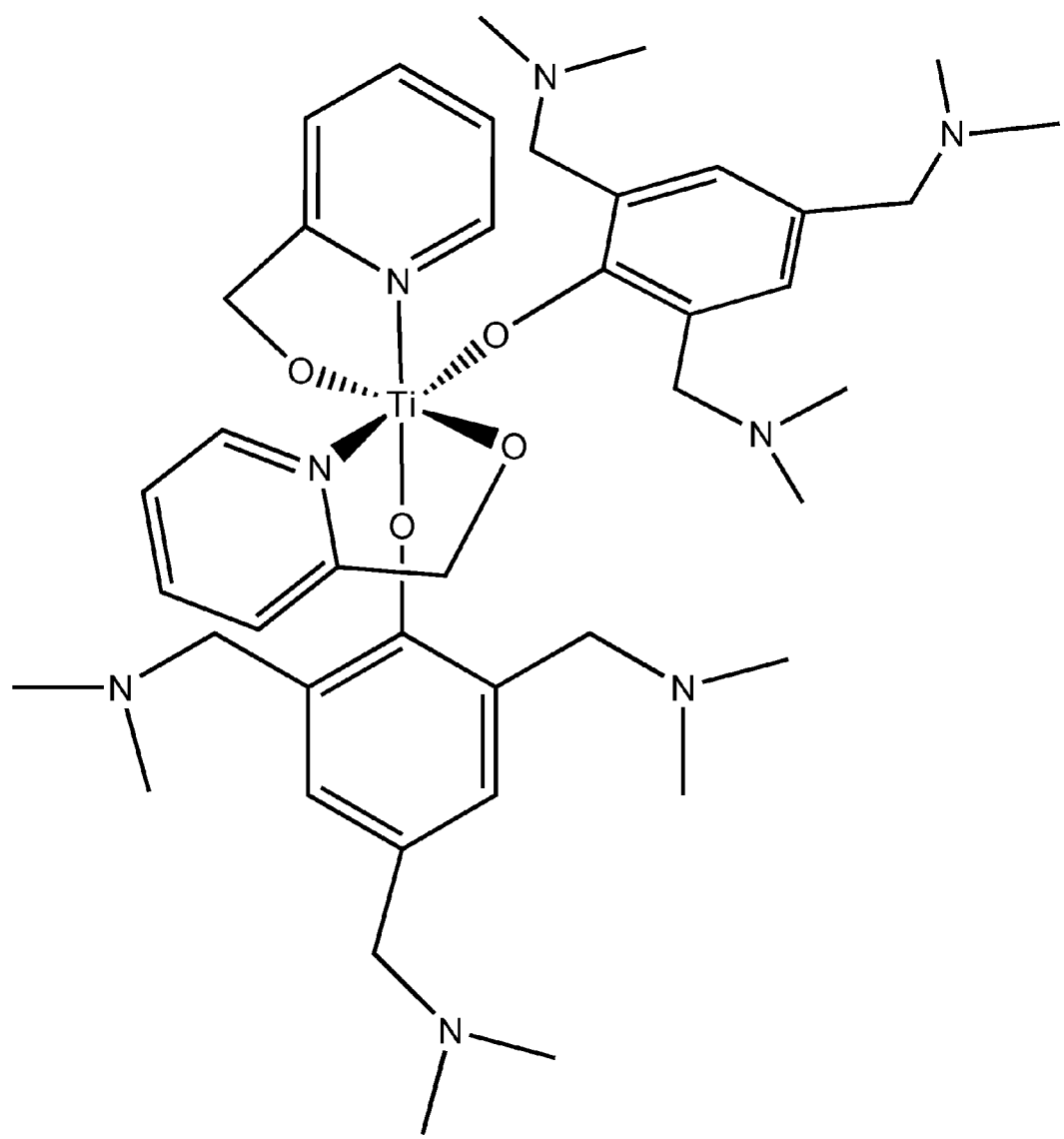
FIG. 1 illustrates the structure of $(OC_6H_6N)_2Ti(OC_6H_2(CH_2N(CH_3)_2)_3-2,4,6)_2$.

The present invention relates to a specific metal alkoxide composition and structure, represented by the chemical formula $(OC_6H_6N)_2Ti(OC_6H_2(CH_2N(CH_3)_2)_3-2,4,6)_2$, as depicted in FIG. 1. As prepared, the compound is a crystalline substance with a hexavalent titanium atom bonded to two $OC_6H_6N$ groups and two $OC_6H_2(CH_2N(CH_3)_2)_3-2,4,6$ groups with a theoretical molecular weight of 792.8. An elemental analysis was performed with the results showing that the compound comprises 63.6% C, 8.1% H, 14.1% N, 8.1% O and 6.0% Ti.

The bidentate nature of the $OC_6H_6N$ (referred to herein as OPy) group, the steric bulk of the $OC_6H_2(CH_2N(CH_3)_2)_3-2,4,6$ (referred to herein as TAP) ligand, and the amino functionality of the $OC_6H_2(CH_2N(CH_3)_2)_3-2,4,6$ ligand combine to effectively limit conventional hydrolysis of the alkoxide while maintaining solubility in aqueous media. Therefore, unlike many other similar compounds, the compound of the present invention is both water soluble and stable in an aqueous solution.

The heteroleptic, mononuclear $(OC_6H_6N)_2Ti(OC_6H_2(CH_2N(CH_3)_2)_3-2,4,6)_2$ was synthesized from the iso-propoxide derivative via alcoholysis exchange based upon known procedures. The previously established validity of the alcoholysis exchange process on the $(OC_6H_6N)_2Ti$ moiety coupled with solution-NMR (proton) results that confirm the presence of the $(OC_6H_6N)$ and $OC_6H_2(CH_2N(CH_3)_2)_3-2,4,6$ moieties, support the successful formation of the monomeric $(OC_6H_6N)_2Ti(OC_6H_2(CH_2N(CH_3)_2)_3-2,4,6)_2$ complex. The monomeric $(OC_6H_6N)_2Ti(OC_6H_2(CH_2N(CH_3)_2)_3-2,4,6)_2$ as-synthesized material exists as an oil, precluding a full structural determination from a solid-state s-ray diffraction analysis.

In one embodiment, a stock solution of $(OPy)_2Ti(TAP)_2$ was generated by dissolving 0.048 g of the $(OPy)_2Ti(TAP)_2$ material into 2 mL of anhydrous pyridine, producing a 30 mM concentration, under glove box conditions. This solution was stirred for 30 minutes prior to use to ensure proper mixing. Following mixing of the solution, thin films of the material were obtained by spin coating; 0.35 mL of solution was deposited onto a 1×1 inch$^2$ fused silica substrate, and spun at 350 rpm for 30 seconds. Spun films were retained in the glove box for 4 days to allow for the evaporation of any residual pyridine from the film.

The inhibition of hydrolysis at ligand sites even when the molecule is dispersed in water is attributed to steric constraints imposed by the bidentate pyridine carbinoxide (OPy) and monodentate tri-amino-phenoxide (TAP) groups. It is believed that the amino groups present on the TAP ligand further facilitate water solubilization through H-bonding with the water. The inert character of the molecule to conventional hydrolysis chemistry enables an evaluation of photoexcitation as a means to influence the evolution of intermolecular bond formation.

Figure 2:
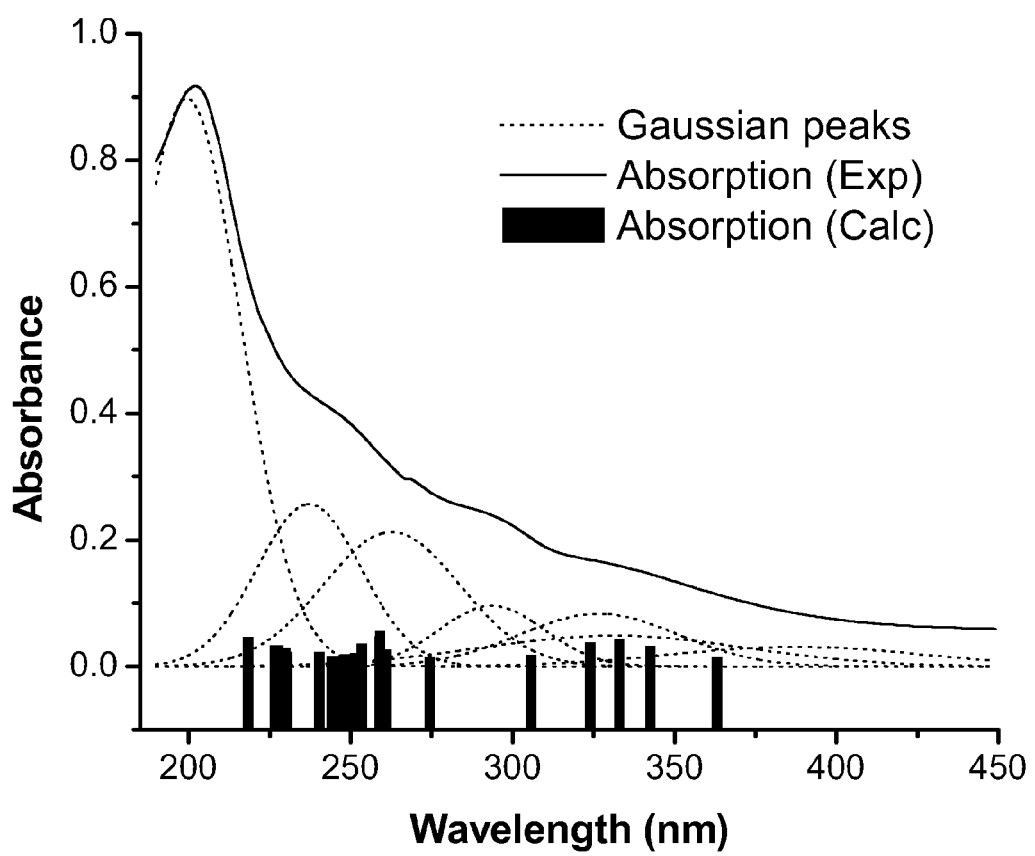
FIG. 2 shows the UV-vis absorption characteristics of $(OC_6H_6N)_2Ti(OC_6H_2(CH_2N(CH_3)_2)_3)_3-2,4,6)_2$.

Samples of the Ti-alkoxide material for UV-exposure were prepared by dissolution of $(OPy)_2Ti(TAP)_2$ (106 mM) in anhydrous pyridine (1 mL typical specimen size) under standard inert atmosphere (Ar) conditions (referred to herein as the "stock" solution). Solution samples containing a 4:1 molar ratio of $H_2O$ to Ti (designated "stock (aq)") were also prepared by appropriate water addition to the 106 mM $(OPy)_2Ti(TAP)_2$ (anhydrous pyridine) stock solution. All solutions were contained within fused silica cuvettes (1 cm square cross-section) during optical evaluation. FIG. 2 contains the corresponding solution UV-vis absorption spectra. Included in the figure is the pyridine solvent absorption spectrum and a diluted (10.6 mM alkoxide)) stock(aq) solution spectrum. The lower absorbance of the latter spectrum enables the observation of a broadened resonance at 340 nm, corresponding to the metal-to-ligand charge transfer band in the molecule. In order to characterize intrinsic molecular absorption at photon energies greater than the absorption onset for the pyridine solvent, thin films of precursor material were spin-coat deposited from $(OPy)_2Ti(TAP)_2$ in pyridine (34 mM) at 500 rpm for 30 seconds onto fused silica substrates suitable for UV-vis absorption measurement.

The invention being thus described, it will be apparent to those skilled in the art that the same may be varied. Such variations are not to be regarded as a departure from the spirit and scope of the invention, and all such modifications are intended to be included within the scope of the following claims.

I claim:
1. A compound of the formula $(OC_6H_6N)_2Ti(OC_6H_2(CH_2N(CH_3)_2)_3\text{-}2,4,6)_2$, with a structure given by
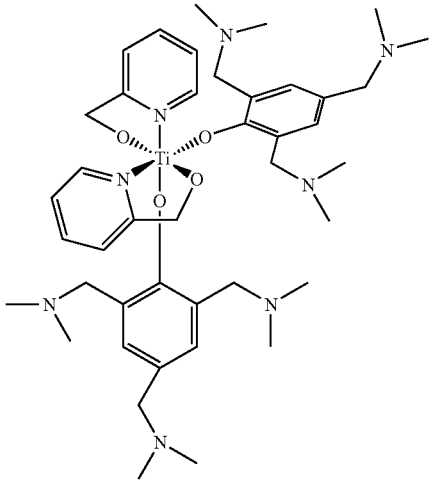
2. The compound of claim 1 having a theoretical molecular weight of 792.8.
3. The compound of claim 1 comprising 63.6% C, 8.1% H, 14.1% N, 8.1% O and 6.0% Ti.
4. The compound of claim 1 wherein the compound is water soluble.
5. The compound of claim 1 wherein the compound is stable in water.
* * * * *